United States Patent
Podhajsky et al.

(10) Patent No.: US 7,979,138 B2
(45) Date of Patent: *Jul. 12, 2011

(54) METHOD AND APPARATUS FOR MONITORING DISC PRESSURE DURING HEAT TREATMENT OF AN INTERVERTEBRAL DISC

(75) Inventors: Ronald J. Podhajsky, Boulder, CO (US); Kristin D. Johnson, Louisville, CO (US)

(73) Assignee: Covidien AG, Neuhausen am Rheinfall (CH)

( * ) Notice: Subject to any disclaimer, the term of this patent is extended or adjusted under 35 U.S.C. 154(b) by 0 days.

This patent is subject to a terminal disclaimer.

(21) Appl. No.: 12/622,984

(22) Filed: Nov. 20, 2009

(65) Prior Publication Data
US 2010/0168732 A1 Jul. 1, 2010

Related U.S. Application Data (63) Continuation of application No. 11/393,249, filed on Mar. 30, 2006, now Pat. No. 7,627,380.

(60) Provisional application No. 60/666,829, filed on Mar. 31, 2005.

(51) Int. Cl.
*A61N 1/04* (2006.01)

(52) U.S. Cl. .......................................... 607/99; 607/117
(58) Field of Classification Search .................... 606/32, 606/49; 607/98, 99, 116, 117
See application file for complete search history.

(56) References Cited

U.S. PATENT DOCUMENTS

| | | | |
|---|---|---|---|
| 5,433,739 | A | 7/1995 | Sluijter et al. |
| 6,604,003 | B2 | 8/2003 | Fredricks et al. |
| 7,267,683 | B2 | 9/2007 | Sharkey et al. |
| 2002/0138091 | A1 | 9/2002 | Pflueger |
| 2003/0028147 | A1 | 2/2003 | Aves et al. |
| 2004/0015218 | A1 | 1/2004 | Finch et al. |
| 2005/0277918 | A1 | 12/2005 | Shah et al. |
| 2006/0064145 | A1 | 3/2006 | Podhajsky |
| 2006/0206131 | A1 | 9/2006 | Conquergood et al. |

*Primary Examiner* — Lee S Cohen (57) ABSTRACT

A probe system and method for treating an intervertebral disc of a patient are disclosed. A probe has a cannula having an open end defined at a distal end and adapted to couple to a power source. A stylet fits into the cannula so that a distal end of the stylet occludes the open end at the distal end of the cannula. The probe system also includes a pressure monitoring apparatus coupled to the stylet, with the stylet including a pressure sensor in proximity to the distal end of the stylet. The pressure sensor communicates with the pressure monitoring apparatus to measure the pressure of the intervertebral disc. The power source delivers power to the distal end of the cannula, causing heating of the disc when the distal end of the cannula is disposed within the disc, thereby relieving patient pain associated with the disc.

11 Claims, 6 Drawing Sheets

METHOD AND APPARATUS FOR MONITORING DISC PRESSURE DURING HEAT TREATMENT OF AN INTERVERTEBRAL DISC

CROSS-REFERENCE TO RELATED APPLICATIONS

This application is a continuation of U.S. patent application Ser. No. 11/393,249 filed on Mar. 30, 2006, now U.S. Pat. No. 7,627,380 issued on Dec. 1, 2009, which claims the benefit of and priority to U.S. Provisional Application No. 60/666,829, filed on Mar. 31, 2005, the entire contents of each of which are incorporated herein by reference.

BACKGROUND

1. Technical Field

The present disclosure relates to a method and apparatus for treating an intervertebral disc for relief of back pain. More particularly, the present disclosure relates to a method and an apparatus for measuring pressure of an intervertebral disc during heating.

2. Description of Related Art

The curing of back pain is one of the most important objectives of neurosurgeons, orthopedists, anesthesiologists and neurologists. Back pain is one of the most common forms of pain and accounts for huge amounts of disability and loss of labor throughout the world. The curing of back pain heretofore has been in the domain of surgery, percutaneous injection of chemicals into the intervertebral disc, percutaneous removal by mechanical means of intervertebral discs, RF heating of peripheral nerves outside of the intervertebral disc to interrupt nerve fibers outside of the disc, and various forms of drug and rehabilitation therapy.

The use of radiofrequency (RF) electrodes and power sources for generators is common in the field of neurosurgery, anesthesiology, and cardiology for the destruction of neural tissue. This is typified by the RF electrodes and RF lesion generator systems of Integra Radionics, Inc. in Burlington, Mass., USA. Heretofore, the lesion electrodes are placed at the target site under various types of guidance, including stimulation, x-ray control, tomographic image control, and stereotactic apparatus. The electrode typically consists of an insulated shaft with an exposed tip which is elevated to radiofrequency potential. A second electrode, usually a dispersive electrode with a large area, is placed elsewhere on the body to return the radiofrequency current to the RF generator, thereby making the patient's body part of the radiofrequency circuit. The intensity of radiofrequency current at the exposed tip of the radiofrequency lesion electrode causes the heating of the tissue in the neighborhood of the electrode, and thus the destruction of that tissue. Typically, the tissue has always been either direct neurological tissue, such as in the brain or the spinal cord, or muscle tissue, as in the heart in the case of cardiac ablation.

A typical example of radiofrequency lesion making is for the relief of various types of back pain, as in the case of facet denervation or in direct destruction of low back nerve structures such as the sympathetic nerves or communicating rami. In the case of facet denervation, the electrode is placed near a small nerve branch which innervates the spinal facet joints and a heat lesion is made which interrupts the noxious signals emanating from these joints. RF heating is also used for destruction of ganglia such as the sphenopalatine ganglion or of other nerves which are ramifications of the nerves which exit from the spinal column. The mechanism is a direct interruption of nerves and thus of the pain signals from the affected areas to the spinal cord. These procedures have been effective; however, there are many pain syndromes which relate to the region around the intervertebral disc itself. It is very difficult to achieve a comprehensive destruction of the nerves which innervate the disc. This is because the disc is innervated by multiple nerve branches. Some of these branches lie close to the exiting spinal nerves, notably those which innervate the clinically important posterior part of the disc. Destruction of these branches with a heat lesion would therefore carry the risk of damaging the spinal nerves. It would be a very effective treatment for so-called discogenic back pain to be able to simply and with a minimal number of percutaneous needle sticks denervate or destroy the numerous nerve structures which are present at the surface of the entire disc without endangering the important nerve structures inside and exiting from the spinal canal.

It has been a characteristic of RF lesion making in the nervous tissue or in the soft muscle tissue that the RF electrode, which affects the heating, be placed in proximity to the tissue to be destroyed. That is, by various stereotactic means such as X-ray, fluoroscopy, computerized tomography (CT) guidance, magnetic resonance (MR) guidance, or stimulation and recording, the tip of the RF electrode is placed directly on or very near the target nerves themselves and the heating is subsequently carried out.

As alluded to above, one of the outstanding problems in the treatment of back pain relates to neural structures that innervate the intervertebral disc itself. There are numerous sensory nerves which cluster at the exterior surface of the intervertebral disc and sense mechanical deformations of the disc. These nerves appear to protect against excessive stress of the disc wall, which in turn may cause serious damage to the disc, such as rupture, bulging, or herniation. In the situation of an overstressed disc, a rupture can cause extrusion or bulging of the inner material of the disc beyond the external wall with consequent pressure on nerves in the vicinity. This is one of the most common forms of back pain and usually must be cured by surgery or percutaneous disc removal. However, another very common form of back pain related to the disc is the mere irritation or stimulation of the numerous small nerves that innervate the periphery of the disc and sense its mechanical stress. These nerves are found ubiquitously over the surface of the disc. In the situation where herniation or extrusion of the disc has not taken place, yet these numerous tiny nerves are stimulated to produce a painful response, there is no simple surgical treatment and the patient may be in extreme pain and distress as a result. It may be fruitless to attempt to place an RF electrode directly on these small nerves, as they are distributed over an extensive surface of the disc, making it impractical and dangerous to introduce a sufficient number of electrodes in to denervate all of them. More particularly, it is not possible to know beforehand exactly which of these sensing nerves is causing the problem. Indeed, there may be a large number of them over the entire surface of the disc in the situation that the disc is extremely distorted, or alternatively, only a subset of them at one particular location for a more focal disc bulge.

U.S. Pat. No. 5,433,739 issued to Sluitjer et al. on Jul. 18, 1995 describes a technique of introducing an RF electrode or other heating electrode into the intervertebral disc, typically under fluoroscopic control, and heating the entire disc to a temperature significantly above body temperature. The heated disc heats the nerves which innervate its surface, and the nerves are destroyed or altered when the heat of the disc is elevated to an appropriately high temperature. The nerves are heated and desensitized around the disc by minimal invasion to the body, while at the same time sparing the larger nerve bundles running in the vicinity of the disc. This technique produces significant pain relief in a substantial fraction of patients suffering from back pain. Additionally, an indirect radiofrequency lesion method is described whereby the destruction of desired neural structures is done not by direct placement of an RF electrode near the structures, but rather by the radiofrequency heating of an intermediate structure, which in turn diffuses the heat to the neural structures in a more diffuse and global fashion.

Associated with indirect or global radiofrequency heating techniques, it is important to be able to monitor pressure, not only at the direct point of RF electrode heating, but also at remote points in space so as to monitor and control the progress of decreased tissue volume. Thus, there remains a need to provide intervertebral pressure monitoring systems to carry out the direct and/or indirect monitoring of points in space relative to the primary RF lesion electrode for safer and more effective control of the heating process.

SUMMARY

The present disclosure is directed to a probe system for treating an intervertebral disc of a patient, including: a probe, with the probe having a cannula with a proximal end and a distal end and having an open end defined at the distal end thereof, and with the cannula adapted to couple to a power source. The probe also has a stylet having a proximal end and a distal end, with the stylet fitting into the cannula so that the distal end of the stylet occludes the open end at the distal end of the cannula. The probe system also includes a pressure monitoring apparatus adapted to be coupled to the stylet, with the stylet including a pressure sensor in proximity to the distal end of the stylet, with the pressure sensor adapted to communicate with the pressure monitoring apparatus so as to measure the pressure of the intervertebral disc. The power source delivers power to the distal end of the cannula, causing heating of the disc when the distal end of the cannula is disposed within the disc, thereby relieving patient pain associated with the disc.

The pressure sensor may be disposed in an aperture defined in proximity to the distal end of the stylet, and the pressure sensor may be at least partially exposed through the aperture in the stylet, to sense pressure in the disc thereby. The stylet may have a tip at the distal end of the stylet. The tip of the stylet may have an aperture defined therein, and the pressure sensor may be at least partially exposed through the aperture at the tip, to sense pressure in the disc thereby. The cannula may be substantially insulated on a surface of the cannula in communication with the body of the patient including the intervertebral disc. The cannula may have an uninsulated electrically conductive tip at the distal end of the cannula. The uninsulated electrically conductive tip may be adapted to couple to the power source such that when the distal end of the cannula is within the disc, power can be transmitted to heat the disc.

The probe system may further include an impedance monitoring apparatus adapted to be coupled to the stylet by an electrical interface to monitor the tissue impedance of the patient to confirm the proper placement of the distal end of the cannula inside of the disc. The probe system may further include a temperature monitoring apparatus adapted to be coupled to the stylet. The stylet may include a temperature sensor in proximity to the tip of the stylet. The temperature sensor may be capable of communicating with the temperature monitoring apparatus by an electrical connector interface to measure the temperature of the temperature sensor near the disc. The temperature sensor may be adapted to communicate with the temperature monitoring apparatus so as to measure the temperature of the intervertebral disc when the tip of the stylet is disposed in proximity to the disc.

The present disclosure relates also to a method of treating back or neck pain of a patient by heating an intervertebral disc. The method includes providing a probe having a proximal end and a distal end, with the distal end having a tip. The probe may be operatively coupled to a power source. The method also includes providing a pressure sensor in proximity to the tip of the probe and a pressure monitoring apparatus operatively coupled to the pressure sensor via the probe. The method also includes delivering power from the power source to the distal end of the probe, causing heating of the disc when the distal end of the probe is disposed within the disc, to relieve patient pain associated with the disc thereby, and measuring pressure of the disc. The step of delivering power from the power source to the disc via the probe may be performed for a period of approximately one minute. Immediately following the step of delivering power from the power source to the disc via the probe, the method may further include the step of turning off the power. Following the step of turning off the power, the method may further include the steps of waiting for a period of approximately one minute and measuring the pressure sensed by the probe pressure sensor. If it is determined that further treatment is necessary based upon the measured pressure in that a substantial change in disc pressure to a pressure level below a threshold pressure has not been achieved, the method may further include the step of re-delivering power from the power source to the disc via the probe causing heating of the disc. The probe may be a radiofrequency electrode and the power source may be a radiofrequency generator, and the method may further include the steps of increasing voltage output of the radiofrequency generator so as to send current through the radiofrequency electrode into the disc and thus heat the disc by ohmic heating, and decreasing the voltage output of the radiofrequency generator after a change in disc pressure has been measured.

The pressure sensor may be disposed in proximity to the tip of the distal end of the probe. The probe may have an aperture disposed such that the pressure sensor is at least partially exposed through the aperture in the probe, thereby to sense pressure in the disc. The pressure sensor may be disposed at the tip of the distal end of the probe. The probe may have an aperture disposed such that the pressure sensor is at least partially exposed through the aperture, thereby to sense pressure in the disc.

The present disclosure relates also to a method of treating back or neck pain of a patient by heating the interior of an intervertebral disc. The method includes providing a probe. The probe may have a proximal end and a distal end having a tip. The probe may be operatively coupled to a power source. The method includes also the steps of providing a pressure sensor at the distal end at or in proximity to the tip of the probe and a pressure monitoring apparatus operatively coupled to the pressure sensor via the probe; inserting the probe into the patient so that the tip at the distal end of the probe is positioned inside the intervertebral disc. The method also includes the steps of delivering power via the probe to the probe tip so as to heat tissue around the probe tip when the probe tip is in the intervertebral disc so that the probe tip causes heating of the interior of the intervertebral disc to a temperature substantially above body temperature by absorption of at least a portion of the power delivered via the probe tip to the tissue of the intervertebral disc, thereby causing heating and resultant changes in the disc material and nearby neurological structures to relieve the patient's pain, and monitoring pressure of the intervertebral disc by reading output of the pressure monitoring apparatus operatively coupled to the pressure sensor, and thereby quantitatively monitoring the heating process of the intervertebral disc. The step of delivering power may be performed for a period of approximately one minute. Immediately following the step of delivering power, the method may further include the step of turning off the power. Following the step of turning off the power, the method may further include the steps of waiting for a period of approximately one minute and reading the output of the pressure monitoring apparatus operatively coupled to the pressure sensor. If it is determined that further treatment is necessary based upon the measured pressure in that a substantial change in disc pressure to a pressure level below a threshold pressure has not been achieved, the method may further include the step of re-delivering power from the power source to the disc via the probe causing heating of the disc.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

The present disclosure will be understood more fully from the detailed description given below and from the accompanying drawings of particular embodiments of the present disclosure which, however, should not be taken to limit the present disclosure to a specific embodiment but are for explanatory purposes.

Numerous specific details may be set forth herein to provide a thorough understanding of a number of possible embodiments of the present disclosure. It will be understood by those skilled in the art, however, that the embodiments may be practiced without these specific details. In other instances, well-known methods, procedures, components and circuits have not been described in detail so as not to obscure the embodiments. It can be appreciated that the specific structural and functional details disclosed herein may be representative and do not necessarily limit the scope of the embodiments.

Some embodiments may be described using the expression "coupled" and "connected" along with their derivatives. For example, some embodiments may be described using the term "connected" to indicate that two or more elements are in direct physical or electrical contact with each other. In another example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments disclosed herein are not necessarily limited in this context.

It is worthy to note that any reference in the specification to "one embodiment" or "an embodiment" means that a particular feature, structure, or characteristic described in connection with the embodiment is included in at least one embodiment. The appearances of the phrase "in one embodiment" in various places in the specification are not necessarily all referring to the same embodiment.

Embodiments of the present disclosure will be described hereinbelow with reference to the accompanying drawings. In the following description, well-known functions or constructions are not described in detail to avoid obscuring the disclosure in unnecessary detail. In the drawings and in the descriptions which follow, the term "proximal", as is traditional, will refer to the end of the electrode or probe which is closer to the user, while the term "distal" will refer to the end which is further from the user.

RF electrode heating, as described in commonly owned U.S. Pat. No. 5,433,739, and which is hereby incorporated herein by reference in its entirety, destroys neurological structures. To determine the appropriate application of heating to destroy neurological structures and release the correct amount of pressure on a herniated disc, in addition to means for monitoring temperature, or in lieu thereof, a system for measuring the pressure of the disc is included in the heating system of the present disclosure. The system for measuring the pressure in the disc includes a pressure sensor and any ancillary equipment to the pressure sensor. The use of a pressure sensor provides data on the status of the disc during thermal treatment and provides an indication of the progress of tissue volume reduction during the RF procedure. Once there has been a substantial change in disc pressure, the heating procedure can be terminated. "Substantial change in disc pressure" as used herein refers to a tissue volume reduction in the nucleus of the intervertebral disc which relieves the subject of back pain. Thereby, the disc pressure has been reduced to a threshold pressure below which the patient no longer senses back pain.

The pressure sensor can be any type of pressure sensing device suitable for the application. For example, the pressure sensing device may be a strain gauge sensor, an optical strain sensor, or electromechanical sensor. The pressure sensor may be an electromechanical sensor array such as a micro-electromechanical system (MEMS). The pressure sensing device may be included on the RF electrode or may be a separate needle independent of the RF electrode but placed in the nucleus of the disc during the intervertebral heating procedure.

In addition to the pressure sensing device, ancillary equipment is also provided. Ancillary equipment includes equipment capable of providing energy such as a power or light source together with circuitry that is capable of detecting the output of the pressure sensing device and analyzing and/or converting the output into usable information. The pressure sensor measures the intervertebral pressure, converts the pressure measurement into an electrical signal, and transmits the pressure measurement to a display. The output may be displayed to the user in any useful pressure metric such as pounds per square inch (psi), millimeters of mercury (mm Hg), Newtons per square meter ($N/m^2$ or Pascal) or Newtons per square millimeter ($N/mm^2$), kilograms per square centimeter ($kgf/cm^2$), and the like. The output may also serve as an input parameter for a control circuit in the RF generator. For instance, the pressure information would then influence the energy output of the RF generator applied to the electrode. If a certain change in pressure is desired, the pressure output can be used to determine the change in pressure as heat is applied to the intervertebral disc.

In one embodiment of the present disclosure, the ancillary equipment can be included internally to the RF generator. For instance, the pressure sensing device is a transducer contained within the heating system. In another embodiment of the present disclosure, the ancillary equipment can be enclosed in an accessory apart from the generator but connected to the RF electrode. In a further embodiment of the present disclosure, the ancillary equipment can be enclosed in an accessory apart from the RF generator and coupled to a pressure sensing electrode separate from the RF electrode.

Figure 1:
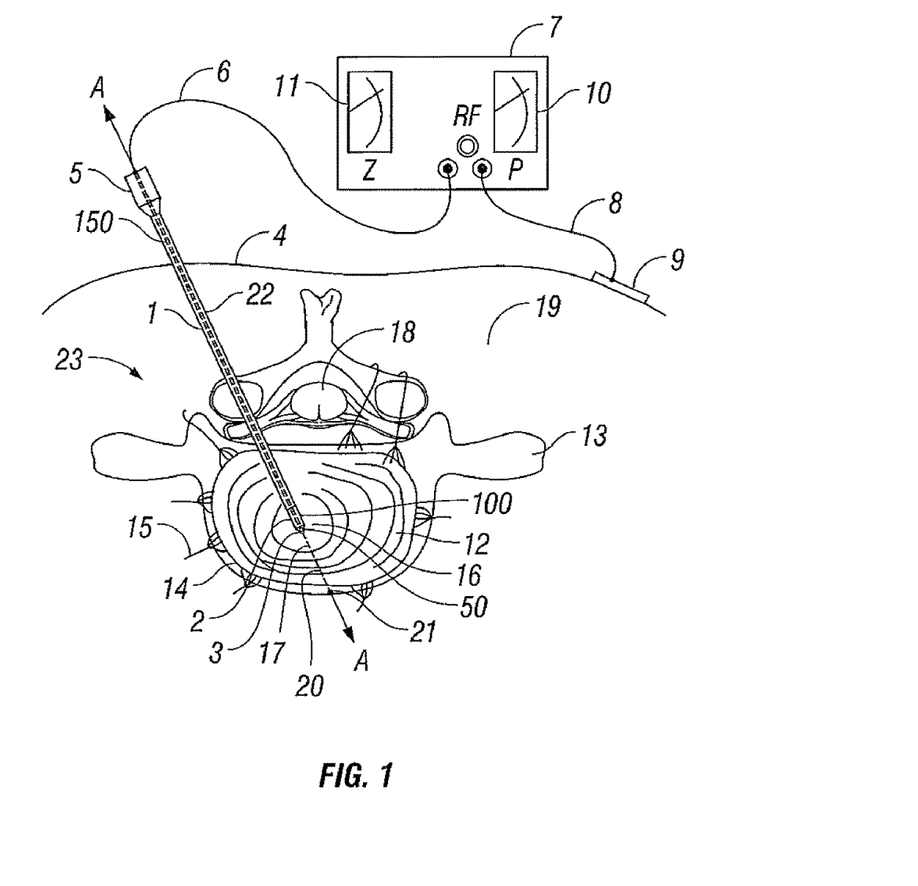
FIG. 1 illustrates RF heating of an intervertebral disc according to the present disclosure, using a single percutaneous electrode.

FIG. 1 shows the method and apparatus of the present disclosure, which involves an indirect heating of neural structures by placement of an RF electrode into the intervertebral disc and a measurement of the pressure in the intervertebral disc, so as to relieve back pain associated with innervation of the surface of the disc or nearby structures. This is merely one embodiment of the present disclosure involving an RF electrode, but could apply equally well to any other probe type which provides heat to the disc. Other systems such as thermal and cryogenic systems described in commonly owned U.S. Pat. No. 5,571,147, which is incorporated herein by reference in its entirety, are included in the present disclosure.

Referring to FIG. 1, the electrode 1 consists of a rigid shaft which is insulated except for its tip end 2. The tip end has a sharpened point 3, enabling it to penetrate the tissue of the body 4 during percutaneous entry. The exposed metal tip 2 represents the active electrode area. At the hub 5 of the electrode, there is a connection cable 6 coupling electrode 1 to a source 7 of radiofrequency power, e.g., an RF lesion generator. This RF lesion generator is typified by the products of Integra Radionics, Inc. in Burlington, Mass., USA. There is also a cable connection 8 to a reference electrode 9 that is typically attached to a surface of the body. This RF lesion connection diagram is referred to as a monopolar type arrangement, meaning that there is a single active electrode tip 2. The reference electrode 9 typically has a very much larger area than the active tip 2, so that there is no heating at the surface of the body where reference electrode 9 is attached. The radiofrequency generator includes devices and readouts for monitoring the pressure at the electrode tip 2. This is illustrated by the pressure monitoring meter 10. Also monitored is the impedance in the RF circuit through the electrodes as indicated by the meter 11. This impedance monitoring is typical of modern RF lesion generators. The space in the intervertebral disc is of a very special structure and consists of a fibrous material with a substantially low electrical impedance. The RF generator may also include a stimulator and control circuitry to vary and monitor the radio frequency power delivered to the electrode 1.

As shown in FIG. 1, the RF electrode tip 2 is placed directly into the anatomical intervertebral disc 12. By their nature, the intervertebral discs act as cushions or shock absorbers between the bony vertebral structures 13. Because they are elastic, their surface 14 is subject to stresses, strains, and even injury if the disc is overstressed by excess weight or improper mechanical movements. Such stresses can give rise to the distortion of the disc and of its surface shape. Such mechanical distortions of the disc are monitored by the nerve structures 15 which are located over the surface 14 of the disc. These neural sensing structures are distributed widely over the surface of the disc and are the first warning signs of an overstressed disc surface. An overstressed disc surface can give rise to bulging, herniation or even rupture, which is one of the most common causes of back pain. Thus, these neural structures 15 provide natural warning detectors that the disc is being overstressed or injured. Frequently, an injured disc will have irritation to its surface and possibly permanent distortion of its surface, which will give rise to chronic and continuous pain signals from the neural structures 15. Frequently, the patient will be normal in all other respects, yet the chronic irritation of the nerves 15 gives rise to chronic and debilitating pain. As mentioned above, it is impractical to consider knocking out each of these neural structures by multiple placement of numerous RF electrodes near each of them, as in the case of a direct RF lesion techniques done in the past.

By placing even a single RF electrode in the interior region at position 16 approximately at the center of the disc and then heating the region of the interior disc by applying RF power there, one essentially achieves a global spread of heat throughout the disc. This heat then causes heating of the neural structures 15 which innervate the surface of the disc. If properly done with the monitoring of at least one of temperature and pressure, this process can denervate the neural structures 15 on a global or semi-global basis and reduce the tissue volume in the disc. The degree of reduction of tissue volume in the disc can be measured by measuring the pressure in the disc. Hence, the patient is relieved of back pain related to stress of the intervertebral disc and its surface.

Heat produced at the core of the intervertebral disc is spread out over a substantial distance throughout the disc so as to heat its periphery. The reason that the heat can spread so effectively to such a long range is that the intervertebral disc material has no vascularity. Because there is no blood flowing in the disc, the usual dramatic convection of heat away from the heated region is reduced essentially to zero. In this respect, the disc is strikingly different from all other RF lesion targets that are heated. Other targets, such as the brain, spinal cord, muscle tissue, etc., are all highly vascular. Thus, the usual diminution of heating at long range associated with heating the brain tissue and muscle tissue is absent.

A second factor which enhances the global heating of the entire disc is that the disc represents essentially a two-dimensional layer between the bony vertebrae above and below it. The bone is a good thermal insulator and also is not as highly electrically conductive as the disc or normal tissue. Thus, the electrical current from the active tip 2 will tend preferentially to spread only throughout the disc, and much less through the bones above and below it. Heating thereby done within the disc is confined to the disc as a consequence of the insulative character of the bones above and below it. Thus, the heat spreads quickly and effectively through the entire disc, raising the entire pancake-shaped structure of the disc to high temperature. The heat flows to the periphery of the disc where it heats the neural structures and other surrounding tissue. It is only at the disc periphery that vascularity or convective flow enters the equation of heat balance, and essentially only there the heat is sinked away rapidly in the annulus of tissue immediately outside the surface of the disc. Thus, one can expect an elevated temperature throughout the disc with a rapid fall-off of temperature as one emerges from the surface of the disc into the surrounding tissue. However, it is just in that critical range of the surface of the disc where the temperature can remain elevated, thereby destroying the innervating structures of the disc, and yet not endangering other critical structures such as the spinal cord 18 that may be in the vicinity of the disc. Any substantial heating of the spinal cord 18 could cause severe danger and injury to the patient, including life threatening neural interruption. However, by the indirect process of heating the non-vascular disc with rapid fall-off of temperature by blood circulation immediately outside the disc, critical neural structures (e.g. the spinal cord 18) and other neural structures (e.g. the anterior and posterior nerve roots) are not injured by this process. The fact that the procedure is safe and effective was not at all obvious a priori in view of the fact that such a large structure is being heated to significantly elevated temperatures.

Figure 1A:
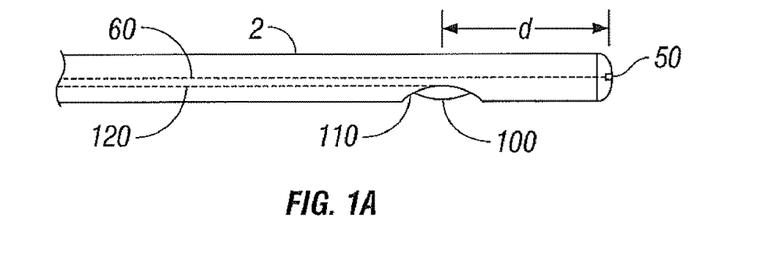
FIG. 1A illustrates a side elevation view of a portion of the single percutaneous electrode of FIG. 1 including a pressure sensor according to the present disclosure.
Figure 1B:
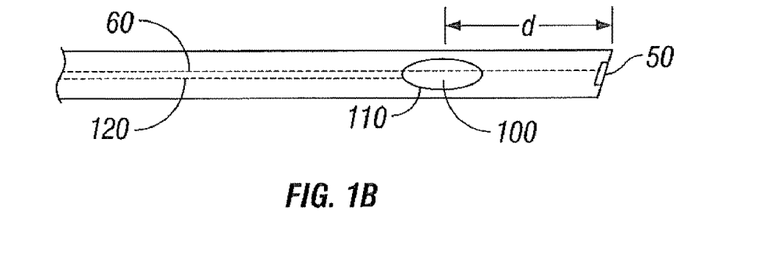
FIG. 1B illustrates a front elevation view of the portion of the single percutaneous electrode of FIG. 1A.

As noted previously, either in addition to monitoring the temperature of the electrode tip, or in lieu thereof, the present disclosure includes the step of monitoring the pressure surrounding the electrode tip. A typical procedure is to place the electrode percutaneously through the surface of the patient's skin 4 under X-ray or fluoroscopic interactive guidance. By taking lateral and anteroposterior views, it is easily ascertained that the proper path of introduction of needle 1 is achieved and that tip 2 resides near the central position 16 of the intervertebral disc. RF current is then applied from the RF generator 7 via the cable 6. Cable 6 can be a multiplexing type cable which includes separate power and instrumentation and control cables to and from the RF generator 7. The current enters the disc, spreads out through the disc material, and returns out through the body to reference electrode 9 and then through the cable 8 back to the RF generator 7. Thus, the patient's body is part of the RF circuit. The pressure at or in the vicinity of the electrode tip 2 is monitored by pressure meter 10. In addition, the temperature at or in the vicinity of the electrode tip is monitored by a temperature meter (not shown). Typically, and as best shown in FIGS. 1A and 1B, monitoring of the pressure in the vicinity of the RF electrode active tip 2 can be implemented by a pressure sensor 100 built into electrode 1 in proximity to RF active tip 2 together with appropriate sensor wires in cable 6 and circuitry in apparatus 7. In particular, the electrode 1 has a central axis "A" extending from a proximal end of the electrode 1 at hub 5 to a distal end of the electrode 1 at tip 2. An aperture 110 is formed and defined in the outer surface of the electrode 1 at a distance "d" extending from the distal end of the electrode 1 at tip 2. Pressure sensor 100 is disposed within the aperture 110 in a recessed position such that the surface of the pressure sensor 100 at least partially exposed by the aperture 110 does not protrude beyond the outer surface of the pressure sensor 100. Typically, the distance "d" is about 0.5 to about 1.0 cm. A pressure sensing cable 120 is coupled to the pressure sensor or transducer 100 and is routed through the multiplexing cable 6 to couple with the pressure monitor 10. In addition, a thermocouple 50 can be disposed at the tip 2 of the electrode 1. A temperature sensing cable 60 is coupled to the thermocouple 50 and routed also through the multiplexing cable 6 to couple with the pressure monitor 10.

In particular, pressure sensor instrumentation cable or wire 150 is embedded within the electrode 1 and is coupled to the pressure sensor 100 and passes through cable 6 to couple to pressure monitoring meter 10 in RF generator 7.

A typical procedure might involve raising the core temperature of the disc 12 in proximity to the tip 2 at core position 17 to 70° C. or more. There is some fall-off of temperature in the disc out towards the perimeter of the disc at position 21 at the far wall of the disc, but nonetheless the surface of the disc 14 is elevated to substantial temperatures 50° C. or 60° C. and perhaps higher. These are sufficiently high temperatures to denervate the fine nerve endings 15 which cover the surface of the disc, thus relieving the patient of pain, but not inducing any pain during the procedure itself.

The electrical resistance, or impedance, of the intervertebral disc material itself is substantially lower than surrounding tissue, illustrated in FIG. 1 as the medium 19 that surrounds the entire spinal column 23. Thus, in the progression of introducing the electrode 1 through the body surface 4, one observes an impedance which is initially relatively high. Then as one enters the disc space, one sees an immediate reduction of the impedance due to the lower electrical resistance of the intervertebral disc 12 itself. This transition between the normal tissue and intervertebral tissue is direct evidence that the sharpened point 3 and RF active tip 2 of the electrode 1 is in the disc 12, and thus in a proper position. Furthermore, when the probe electrode 1 is advanced along a path indicated by the dotted line 20 to the point 21 where the RF active tip 2 has reached the far wall of the disc at point 21, one can again observe an increase of impedance. This increase indicates that the tip 2 of the electrode 1 is emerging from the other side of the disc 12. Thus, one has by impedance monitoring a direct measure of introduction of probe electrode 1 into the disc 12 and the total traversal and limits of the probe tip 2 in the disc space interior region 16.

More particularly, an example of a method of using pressure monitoring in a feedback loop as a control parameter in conjunction with temperature monitoring may include the following steps: a) provide the probe or probe electrode 1 which is operatively coupled to a power source represented by RF generator 7, the probe having a proximal end, represented by the hub 5, and a distal end, represented by the probe tip 2; b) provide the pressure sensor 100 in proximity to the tip 2 of the probe 1 and a pressure monitoring apparatus, represented by RF generator 7, operatively coupled to power source, also represented by RF generator 7; c) thermally treat the intervertebral disc 12 in the interior region 16 for a duration of approximately one minute; d) turn off power from the RF source 7; e) wait for a period of approximately one minute; f) take a pressure measurement; g) determine if further treatment is necessary based upon the pressure measurement; h) resume thermally treating the intervertebral disc 12 in proportion to the pressure difference by re-delivering power from the power source 7 via the probe or probe electrode 1 to the disc 12. If the desired result is not achieved in that the measured pressure indicates that a substantial change in disc pressure to a pressure level below a threshold pressure below which the patient no longer senses back pain has not been achieved, return to step (c) of thermally treating the intervertebral disc 12 in the interior region 16 for a duration of approximately one minute.

The example of the method of using pressure monitoring in a feedback loop as a control parameter in conjunction with temperature monitoring may also be implemented to treat back and neck pain of a patient by radiofrequency heating of the intervertebral disc 12 of the patient. The method includes the steps of: (a) providing a radiofrequency electrode, e.g., probe or probe electrode 1 having a proximal end, represented by hub 5, and a distal end, represented by the probe tip 2, with the radiofrequency electrode 1 having a substantially insulated shaft 22 with an uninsulated conductive radiofrequency tip, represented by sharpened point 3 and exposed metal tip 2, representing the distal end, and radiofrequency connections at the proximal end, represented by connection cable 6, and electrical connections, represented by pressure and/or temperature sensor and/or power cable or wire 150, between the radiofrequency connections 6 and the radiofrequency tip, with the radiofrequency electrode 1 being adapted to penetrate the body of the patient including the intervertebral disc 12; (b) inserting the radiofrequency electrode 1 into the body of the patient, so that the radiofrequency tip 2 may be placed within the intervertebral disc 12; (e) coupling the external radiofrequency generator 7 to the radiofrequency connection so as to apply a radiofrequency voltage generated by the radiofrequency generator 7 to the radiofrequency tip 2 via the electrical connection 150; (d) increasing the radiofrequency voltage to cause current to flow from the radiofrequency tip 2 into the intervertebral disc 12 when the radiofrequency tip 2 is placed within the intervertebral disc 12, thereby causing the intervertebral disc 12 to heat up and thus cause changes in the intervertebral disc material and nearby neurological structures, thereby relieving the patient of the pain; and (e) inserting the pressure sensor 100 into the disc 12, with the pressure sensor 100 being adapted to monitor pressure in the disc 12, whereby a diagnostic evaluation of the disc can be made by observing pressure changes of the disc from heating caused by the radiofrequency tip 2.

The step of increasing the radiofrequency voltage to cause current to flow from the radiofrequency tip 2 into the intervertebral disc when the radiofrequency tip 2 is placed within the intervertebral disc 12 may be performed for a period of approximately one minute. Immediately following the step of increasing said radiofrequency voltage to cause current to flow from the radiofrequency tip 2 into the intervertebral disc 12 when the radiofrequency tip 2 is placed within the intervertebral disc 12, the method may include the step of turning off the radiofrequency voltage. The method may further include the steps of waiting for a period of approximately one minute and measuring the pressure sensed by the pressure sensor probe. If it is determined that further treatment is necessary based upon the measured pressure, the method may further include the steps of: re-coupling the external radiofrequency generator 7 to the radiofrequency connection 6 so as to apply a radiofrequency voltage generated by the radiofrequency generator 7 to the radiofrequency tip 2, and increasing the radiofrequency voltage to cause current to flow from the radiofrequency tip 2 into the intervertebral disc 12 when the radiofrequency tip 2 is placed within the intervertebral disc 12.

The foregoing methods represent an important aspect of the present disclosure related to providing at least one pressure monitoring sensor to confirm the correctness of the procedure following introduction of the probe electrode 1 into the target volume, i.e., the interior region 16 and the far wall of the disc 12 itself.

Another useful target method is using stimulation voltage on the electrode as the electrode is advanced through the tissue and on into the disc. Most lesion generators 7 have a built-in stimulator to stimulate neurological structures. By applying the stimulation as one advances the probe, first through the intervening tissue 19 and then on into the intervertebral disc volume 12, any approximation to critical nerves on that pathway may be detected by continuous stimulation and consequent physiological or motor response. Once the electrode is within the disc volume 12, because there is no innervation of the interior of the disc itself, all stimulated responses are absent.

Figure 2:
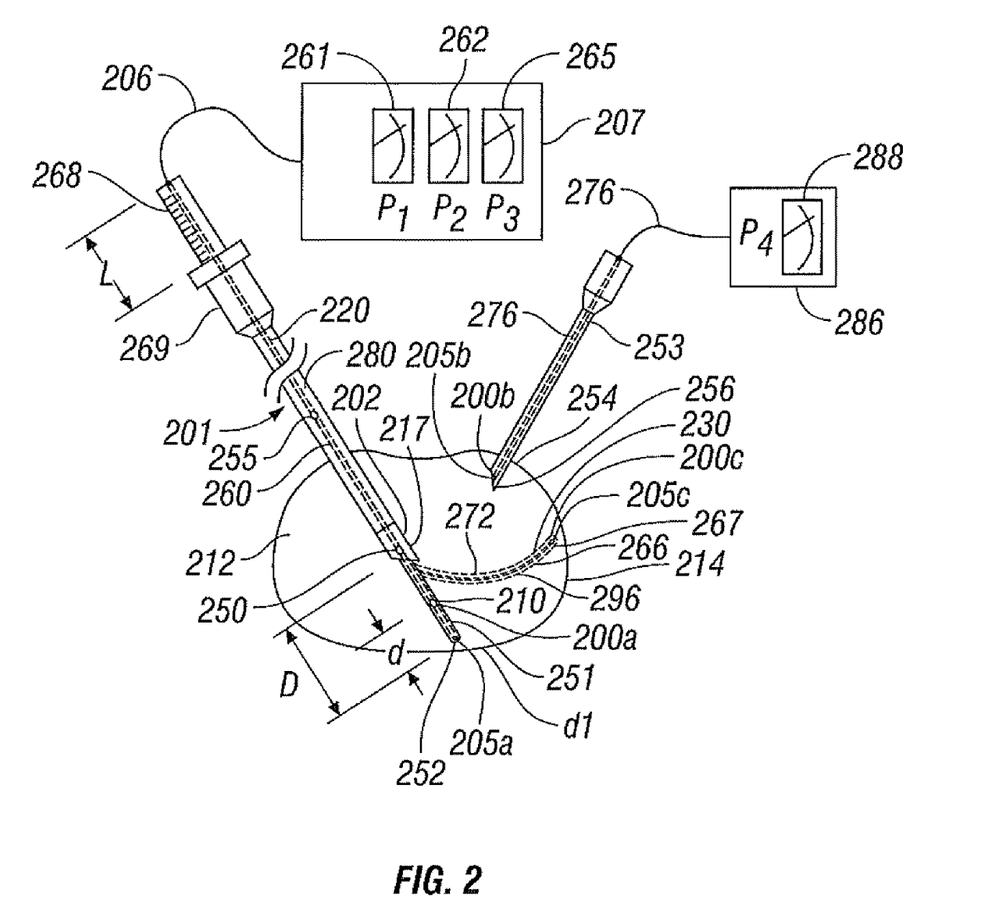
FIG. 2 illustrates an embodiment of the present disclosure involving a heating electrode in the intervertebral disc and secondary pressure sensing probes to monitor positions remote from the primary RF electrode lesion site.

FIG. 2 illustrates embodiments of pressure monitoring at multiple positions associated with the present disclosure. The probe or probe electrode 201 again is inserted into the intervertebral disc space 212. The exposed tip 202 of the probe electrode 201 is positioned at or near the center of the disc 212. The shaft 280 of the electrode, except for the tip 202, is usually insulated to prevent heating of tissue other than that near the probe tip 202. Again, a cable 206, which may be a multiplexing cable, enables application of RF voltage to the probe electrode 201, and thus heating of the core of the disc 212.

Since global heating of the disc 212 occurs to destroy neural structures at long range, monitoring pressure both at the core heating position, namely the point 250 of the electrode tip 202 as well as other points on the surface 214 of the disc 212 provides a user, such as a pain intervention specialist, valuable data on the status of the disc 212. Monitoring of pressure can provide an indication of the progress of tissue volume reduction during the procedure. To illustrate how remote pressure monitoring can be done, an extension 251 emerges from tip 202 of the probe electrode 201 and has a pressure sensor 200a at or in proximity to its tip 252. In a manner as illustrated previously in FIGS. 1A and 1B, the extension 251 includes an aperture 210. Typically, the aperture 210 is formed and defined in the outer surface of the extension 251 at a distance "d" extending from the distal end of the extension 251 at tip 252. The pressure sensor 200a is disposed within the aperture 210 in a recessed position such that the surface of the pressure sensor 200a at least partially exposed by the aperture 210 does not protrude beyond the outer surface of the shaft 280. Again, typically, the distance "d" is about 0.5 to about 1.0 cm. An aperture 250 is disposed in the shaft 280 of the probe or probe electrode 201 such that when the extension 251 is in a retracted position wherein the extension tip 252 is flush with the shaft tip 202, the surface of the pressure sensor 200a exposed by aperture 210 in the extension 251 is also exposed by the aperture 250 in the electrode shaft 280 so that pressure monitoring by the pressure sensor is unimpeded.

Pressure sensor instrumentation cable or wire 260 is embedded within the probe or probe electrode 201 and is coupled to the pressure sensor 200a and passes through cable 206 to couple to pressure monitoring meters 261, 262 and 265 in RF generator 207, which provide readouts for pressure readings P1, P2 and P3, respectively. The tip 252 is shown in proximity to the external surface 214 of the disc 212, and thus the pressure sensor 200a measures the pressure at that point. By this means, the pressure can be monitored not only at the aperture 250 in proximity to which the primary heating is being done, but the pressure also can be monitored at remote point 252 at the surface of the disc 214 which is critical to the denervation of the disc nerves. In addition, a temperature sensor 205a can be disposed at the tip 252 of the electrode extension 251. A temperature sensing cable 220 is coupled to the temperature sensor 205a and also routed through the multiplexing cable 206 to couple with the pressure monitors 261, 262, and 265 within the RF generator 207.

Another method of monitoring pressure of the disc 212 is by having a separate parameter monitoring probe 253 inserted along another route. Typically in a similar manner as described previously with respect to FIGS. 1A and 1B, via pressure sensor 200b located in proximity to tip 256 of the parameter monitoring probe 253, pressure sensor instrumentation cable or wire 276 is embedded within the probe 253 and is coupled to the pressure sensor 200b and couples to pressure monitoring meter 288 in ancillary circuitry 286, providing pressure readout P4. The pressure sensor 200b therefore may measure the pressure at the position 254 at another point on the surface of the disc 212. The probe 253 can be totally insulated so as to reduce perturbations of the radiofrequency current. Alternatively, it can be a second RF electrode used in a bipolar arrangement with the primary electrode 201 or as a secondary primary active electrode in the field of the disc 212. Although ancillary circuitry 286 is shown as a separate device, any remote pressure monitoring sensor may be coupled to a single generator 207 to reduce clutter and to enable a single device to monitor the plurality of monitoring points. In addition, as discussed previously, a temperature sensor 205b can be disposed at the tip 256 of the parameter monitoring probe 253 and used in conjunction with pressure sensor 200b.

It is also possible to move the extension pressure probe 251 backwards and forwards over a range. If the tip 252 of probe extension 251 is extended to a distance "D" beyond the tip 202 to position d1, then the entire distance of that range can be monitored. For example, if pressure meter 261 measures pressure P1 at tip 202 by means of pressure sensor 200a, then pressure meter 262 could measure the pressure P2 at position d1. Similarly, the probe tip 252 may be withdrawn back up inside of the shaft 280 to a position such as at aperture 255. Aperture position 255 is at another point on the perimeter 214 of the disc 212. The pressure sensor 200a, when drawn back to aperture position 255, could monitor pressure P3 at a second point on the perimeter and be visualized on yet another pressure meter 265. The independent probe 253 may be monitored by pressure meter 288 on a separate apparatus or an apparatus combined in the RF lesion generator 207. The single pressure sensor 200a can be configured to transfer the pressure readings to a multiplicity of different pressure meters via a multiplicity of different contact points inside the probe shaft 280 which are independently wired to the multiplicity of different meters such as pressure meters 261, 262, and 265.

Yet another way of measuring the pressure throughout the disc and at remote positions would be to have a side outlet probe 266 with a pressure sensor 200c exposed by an aperture 230 in proximity to the tip 267 of the probe 266, with the aperture 230 being disposed in a similar manner as explained previously with respect to FIGS. 1A and 1B. Pressure sensor instrumentation cable or wire 296 is embedded within the side outlet probe 266 and is coupled to the pressure sensor 200c and passes through cable 206 to couple to pressure monitoring meters 261, 262 and 265 in RF generator 207, which, as before, provide readouts for pressure readings P1, P2 and P3, respectively. Such a side probe 266 could emanate along a curved trajectory (as indicated by the dashed line 272) to access and sample pressure at points transverse to the probe axis. The degree of extension of any of these pressure probes could be gauged by the scale 268 on the hub 269 of the electrode 201. In addition, also as discussed previously with respect to FIGS. 1A and 1B, a temperature sensor 205c can be disposed at the tip 267 of the parameter monitoring probe 266 and used in conjunction with pressure sensor 200c.

It may also be possible to implement the electrode 201 to have a curved or flexible tip structure that can access the entire volume of the disc and thus deposit the primary heat at different locations within the disc. This has been illustrated by the TEW electrode of Integra Radionics, Inc. of Burlington, Mass., USA, and could be applied in the context of the present disclosure. Another illustration of such a curved or side extending electrode for RF heating is discussed below with respect to FIG. 5.

Figures 3, 3A, 4:
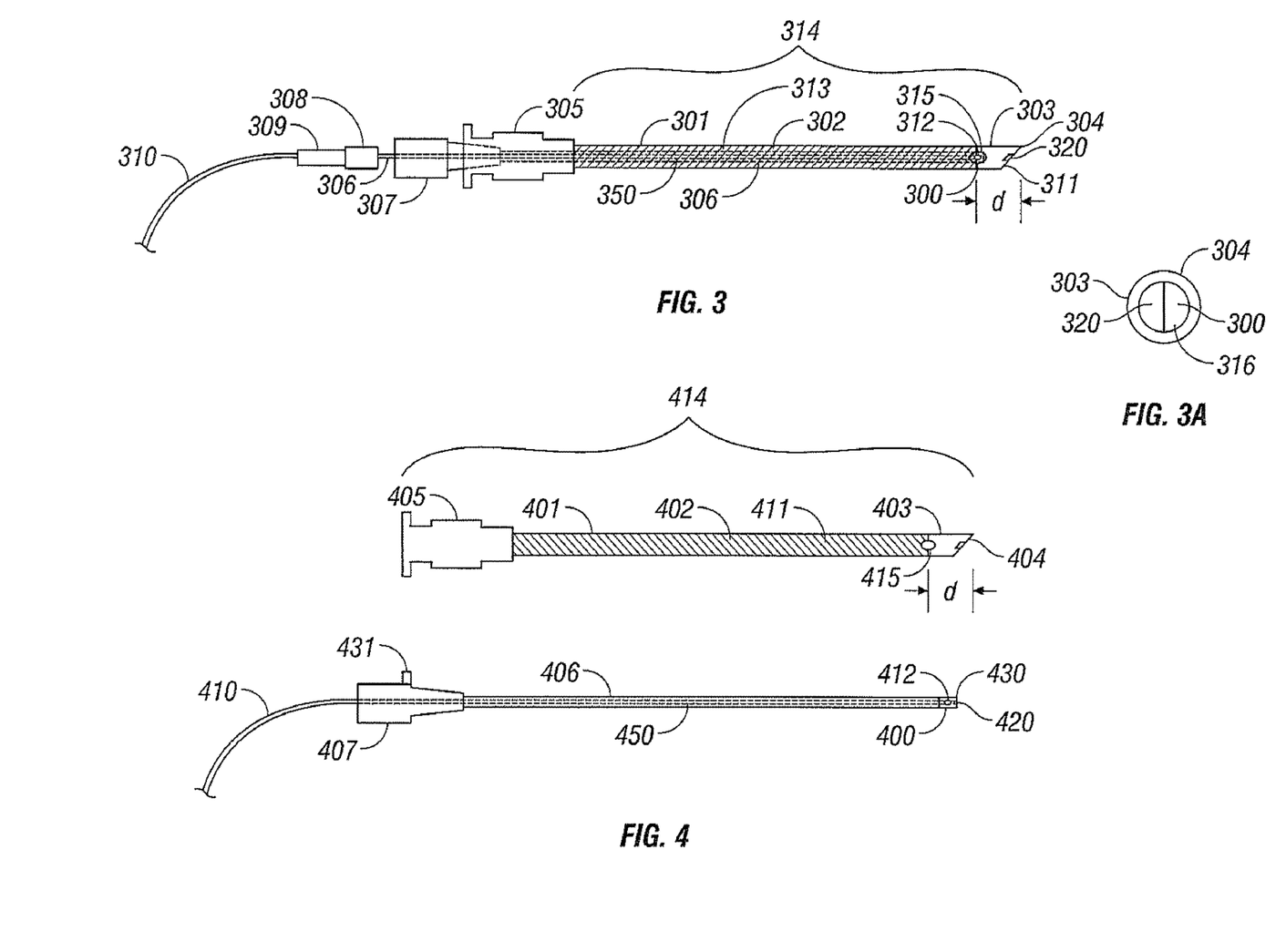
FIG. 3 illustrates an embodiment of the present disclosure of an electrode apparatus for intervertebral disc heating, including special hubs and cable connections and pressure sensing and temperature sensing means.
FIG. 3A illustrates an end view of the electrode apparatus for intervertebral disc heating of FIG. 3 which includes both pressure sensing and temperature sensing means.
FIG. 4 illustrates an embodiment of the present disclosure of a set of apparatus for intervertebral disc heating, including a radiofrequency cannula with insulated shaft, exposed tip, and plastic hub, together with a universal stylet which has external connection means and impedance monitoring means, and pressure sensing means.

There are various embodiments of the needle apparatus which are advantageous to the disc heating procedure. Referring to FIG. 3, there is illustrated a cannula 301 which has an insulated shaft portion 302 (illustrated by the hatched surface) with exposed uninsulated tip 303 that has a sharpened, beveled point 304 for penetration of the body into the disc. The hub 305 of the cannula 301 is made from plastic or low radiopacity material so that imaging along the direction of the needle 314 (which is the combination of the cannula 301 and the hub 305), the so-called "tunnel vision," or "needle view," can be implemented with minimal obstructive artifact from the hub. Further, there is a stylet system which closes off or occludes or obdurates the open lumen (i.e., the open space 313 inside the cannula 301) of the cannula 301 during the insertion and possibly lesioning phase. This stylet shaft is indicated by the dashed line 306, and this shaft 306 extends down to the exposed tip 303 and may or may not have an angled bevel itself so as to appropriately close off the open lumen of tip 303 during the insertion phase. The stylet 306 has a hub 307 which, in this illustrative embodiment, attaches mechanically to the stylet 306. Further, the stylet 306, which may be made from a conductive metal material, has a connection means 308 which can be coupled by cable connector 309 to a cable 310 which can be further coupled to an external apparatus, e.g., a generator, as described above and in FIGS. 1 and 2. The hub 307 again may be made from a plastic material in one embodiment of the disclosure so that the tunnel vision view under X-ray or fluoroscopy can be done with the stylet 306 fully in place in the cannula 301. One has the advantage of a low radiopacity for the majority of the hubs 307 and 305. During the procedure, the cable 310 may be coupled to the external power source, such as RF power source 7, and can supply the radiofrequency or direct current heating power, which emanates through the uninsulated tip 303 into the surrounding bodily tissue (in this case, the intervertebral disc material) to cause frictional heating in that nearby or proximal tissue surrounding the tip 303. In addition, the electrical cable 310 may be used to sense impedance at the electrical tip 303 during the insertion process. That is, because the inner stylet 306 is conductive, it will make electrical contact with the conductive shaft cannula 301, and thereby the tissue impedance of the tissue proximal to the exposed tip 303 may be monitored by appropriate apparatus in the external radiofrequency generating system.

It is also possible that at or in proximity to the tip 311 of the obdurating stylet 306, there can be installed a pressure sensor 300. In particular, in a manner as illustrated previously with respect to FIGS. 1A and 1B, the pressure sensor 300 may be exposed at least partially, such as at an outer surface of the pressure sensor 300, through an aperture 312 in the stylet shaft 306 disposed at a distance "d" upstream from the exposed uninsulated tip 303 at the distal end of the stylet shaft, and further exposed at least partially through a coincident aperture 315 in the cannula 301, thereby enabling the pressure sensor 300 to sense pressure within the disc 212 (see FIG. 2). Pressure sensor 300 instrumentation cable or wire 350 is coupled to the pressure sensor 300 and passes through the stylet 306 either separately from or embedded within cable 310.

Alternatively, or in addition, as illustrated in FIG. 3A, a pressure sensor such as the pressure sensor 300 may be disposed at the exposed uninsulated tip 303 of the stylet shaft 306 and at least partially exposed to the disc 212 (see FIG. 2) via an aperture 316 at the uninsulated tip 303, thereby again enabling the pressure sensor 300 to sense pressure within the disc 212 (see FIG. 2). In addition, also as discussed previously with respect to FIGS. 1A and 1B, a temperature sensor 320 may be disposed at the exposed uninsulated tip 303 of the stylet shaft 306 and used in conjunction with pressure sensor 300 either at the aperture 312 (see FIG. 3) or at the aperture 316 (see FIG. 3A).

Thus, in such a configuration, after appropriate impedance monitoring, X-ray target confirmation, etc., the radiofrequency power can be applied through the cable 310, and the pressure and temperature of the tissue surrounding the tip 303 may be monitored during the heating process by the pressure sensor 300 and the temperature sensor 320.

Those skilled in the art will recognize that RF generator 207 may also serve as a temperature monitoring apparatus which may be adapted to be coupled to the stylet 306 with the stylet including the temperature sensor 320 in proximity to the tip 303 of the stylet 306. The temperature sensor 320 is capable of communicating with the temperature monitoring apparatus represented by RF generator 207 by an electrical connector interface represented by cable connector means 308 which can be coupled by cable connector 309 to cable 310, which may be a multiplexer type cable transporting both power and signal to measure the temperature of the temperature sensor 320 near the disc 212. Therefore, the temperature sensor 320 may be adapted to communicate with the temperature monitoring apparatus represented by RF generator 207 so as to measure the temperature of the intervertebral disc 212 when the tip 303 of the stylet 306 is disposed in proximity to the disc 212.

FIG. 4 shows yet another embodiment of the present disclosure. A needle 414, having a cannula 401 with insulated shaft portion 402 and exposed electrical tip 403 has a hub 405 which is made from a radiolucent material such as plastic. The tip 403 is shown with a beveled point 404 for purposes of illustration. It should be noted that this cannula 401, with open lumen 411, need not have a sharpened point, but rather may be a square, open lumen. In such a situation, the obdurating stylet 406 may have a sharpened point, which will enable effective penetration of the system of cannula 401 plus stylet 406 into the body. The obdurating inner stylet 406, shown as a separate part of this needle system, has in one embodiment a conductive metal shaft. Shown in this figure is a beveled tip 430, which has the same bevel angle as the beveled point 404 of the respective cannula 401. A pressure sensor 400 is disposed at or in proximity to the tip 430. In particular, in a manner as illustrated previously with respect to FIGS. 1A and 1B, an outer surface of the pressure sensor 400 may be exposed through an aperture 412 in the stylet shaft 406 disposed at a distance "d" upstream from the exposed uninsulated beveled tip 430 at the distal end of the stylet shaft 406, and further exposed through a coincident aperture 415 in the cannula 401. Pressure sensor 400 instrumentation cable or wire 450 is coupled to the pressure sensor 400 and passes through the stylet 406 either separately from or embedded within cable 410. In such a situation, the radiolucent hub 407 would have a key 431, which would mate to a corresponding notch (not shown in this figure), such that when the stylet 406 is inserted into the needle 414, the beveled ends of the stylet 406 and the cannula 401 of the needle 414 will be at the corresponding angle, such that the tip of the combination set is flush as it presents to the patient's tissue. In addition, also as discussed previously with respect to FIGS. 1A and 1B, a temperature sensor 420 can be disposed at the exposed uninsulated beveled tip 430 of the stylet shaft 406 and used in conjunction with pressure sensor 400. Again, the stylet 406 is illustrated with a connection cable 410 coupled to the pressure sensor 400, and the cable 410 may further be coupled to external apparatus such as a pressure monitoring apparatus and optionally, impedance monitoring, stimulation, radiofrequency or high-power heating, and a temperature monitoring apparatus.

Figure 5:
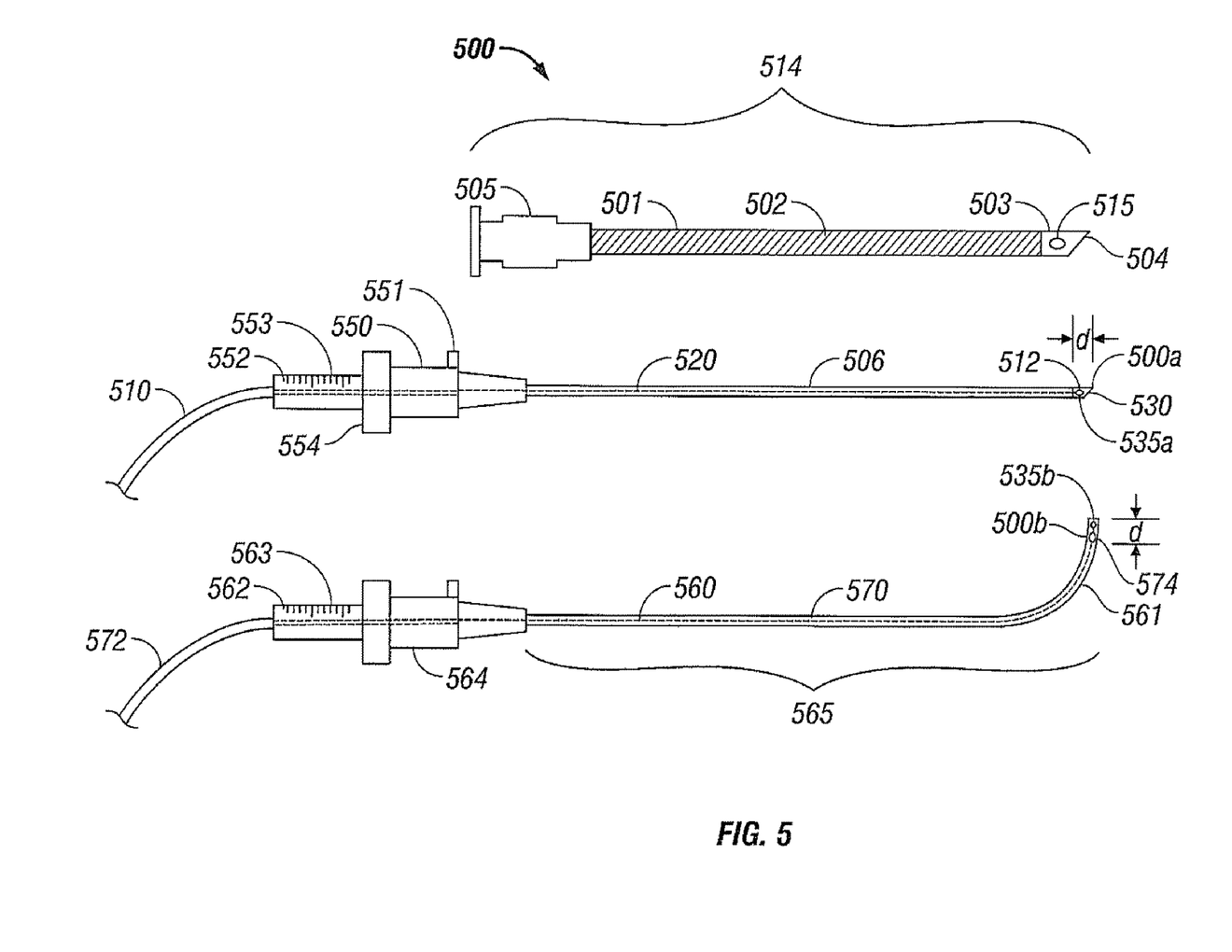
FIG. 5 illustrates an embodiment of the present disclosure of a set of cannula plus straight and curved electrodes and pressure sensing means to make axial or off-axis heating patterns in disc lesioning.

FIG. 5 shows yet another apparatus embodiment of the present disclosure. Again, it is a set of instruments which have appropriate design for the disc heating application. Probe or probe electrode 500 comprises cannula 501 having insulated shaft 502, with exposed tip 503 and sharpened point 504. Again, a radiolucent hub 505 is coupled to the cannula 501. Needle 514 is comprised of the combination of the cannula 501 and the hub 505. Also shown is a straight, multi-purpose stylet 506 with appropriate beveled point 530. A pressure sensor 500a is disposed at or in proximity to the beveled point 530. In particular, in a manner as illustrated previously with respect to FIGS. 1A and 1B, an outer surface of the pressure sensor 500 may be exposed through an aperture 512 in the stylet shaft 506 disposed at a distance "d" upstream from the exposed uninsulated beveled tip 530 at the distal end of the stylet shaft 506, and further exposed through a coincident aperture 515 in the cannula 501. Pressure sensor 500a instrumentation cable or wire 520 is coupled to the pressure sensor 500a and passes through the stylet 506 either separately from or embedded within cable 510. When this stylet 506 is inserted appropriately, the bevels 530 and 504 line up so that they are flush and present a smooth surface to the tissue that is being penetrated. There is an outer hub 550 which is of radiolucent material and has the key 551 that is timed or aligned with an associated slot in the needle hub 505 (said slot is not shown in FIG. 5) so that the bevels 504 and 530 will line up appropriately. Further, it has a secondary adjustable hub 552 which is made of radiolucent material and is imprinted with visible measuring markers 553. The user, by observing these measuring markers 553 relative to, for example, the proximal face 554 of the outer hub 550, may be able to determine, while the electrode is in place in the body, the degree of extension of the beveled point 530 of the stylet 506 relative to the sharpened point 504 of needle 514. In addition, also as discussed previously with respect to FIGS. 1A and 1B, a temperature sensor 535a can be disposed at the exposed uninsulated beveled tip 530 of the stylet shaft 506 and used in conjunction with pressure sensor 500a. This measurement capability would be appropriate for the geometry shown previously in FIG. 2 where the extension 251 may be extended beyond the tip 202 of shaft 280 of the needle so as to make pressure measurements and optionally, extended lesions or extended impedance measurements within the disc 212 itself. Thus, the straight stylet structure shown in FIG. 5 is analogous to the straight stylet structure shown in FIG. 4, with the exception that it has the depth gauge adaptation. In addition, a cable means 510 is also illustrated for connection to the external apparatus.

Further in FIG. 5 is shown a stylet 565 with shaft portion 560 and a curvilinear distal or end portion 561. The curvilinear configuration of the distal end 561 may be either permanently set into the stylet 565 or may be steerable by adaption means on the primary hub 564. Primary hub 564 is analogous or identical to the hub 550 of the straight stylet 506. Again, depth gauge means 562, with depth markers 563, are provided for the operator to gauge the degree of extension of the curved tip 561. A pressure sensor 500b is disposed at or in proximity to the distal end portion or tip 561. In particular, in a manner as illustrated previously with respect to FIGS. 1A and 1B, an outer surface of the pressure sensor 500b may be exposed through an aperture 574 in the stylet shaft 560 disposed at a distance "d" upstream from the exposed uninsulated curved tip 561 at the distal end of the stylet shaft 560. Pressure sensor 500b instrumentation cable or wire 570 is coupled to the pressure sensor 500b and passes through the stylet 565 either separately from or embedded within cable 572. In addition, also as discussed previously with respect to FIGS. 1A and 1B, a temperature sensor 535b can be disposed at the exposed curved tip 560 of the stylet shaft 560 and used in conjunction with pressure sensor 500b. The gauging of the degree of extension of the curved tip 561 would be exemplified by the illustration of FIG. 2 for extended off-axis measurements or heating. Such off-axis heating would be appropriate when difficult approaches to the disc 212 are required. An example of this would be the L5-S1 disc, which, in some cases, requires the needle to be placed in a direction that is not passing through the center of the disc. In such a situation, the needle tip 504 may be off-center from the disc, yet the side extension curve, such as 561 of the stylet 565, may be directed off-axis to bring the average center of lesioning back to approximately the center 250 of the disc 212. This combination of instruments in FIG. 5 represents yet another apparatus embodiment which would be, suitable for the disc heating procedure.

Figure 5A:
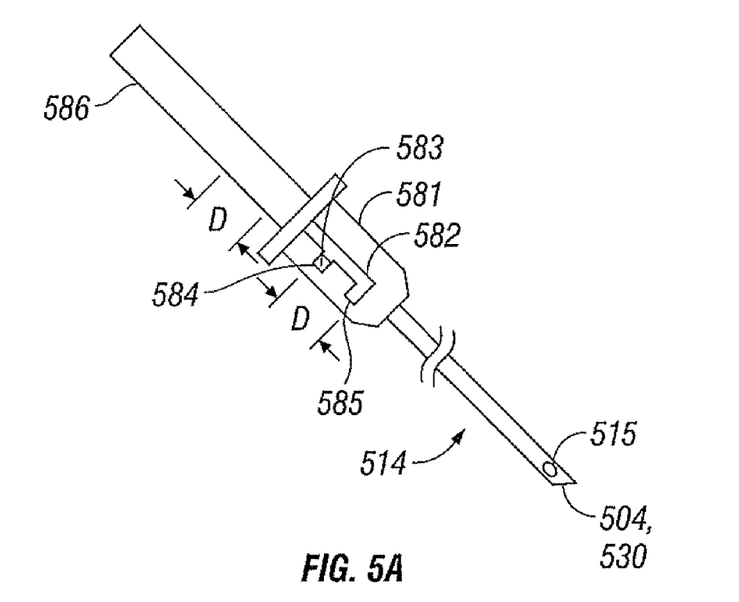
FIG. 5A illustrates a variation of an embodiment of the present disclosure of FIG. 5 of a set of cannula plus straight and curved electrodes and pressure sensing means and a position control device to monitor positions of the heating electrode tip with the electrode tip in a retracted position.
Figure 5B:
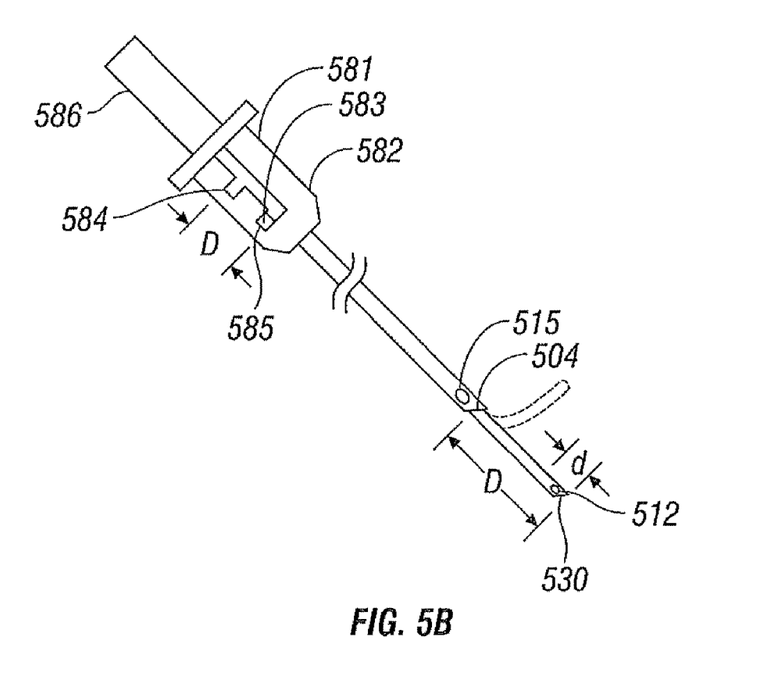
FIG. 5B illustrates the variation of the embodiment of the present disclosure of FIG. 5A with the electrode tip in an extended position.

Still another way of measuring the pressure throughout the disc and at remote positions would be to have a keyed slot in the hub of the probe such that the probe is then moved a fixed distance each time that the key is positioned within the slot. More particularly, FIGS. 5A and 5B illustrate needle 514 of FIG. 5 being comprised of a hub 581 having a key slot 582 extending along a portion of the length of the hub 581, with the key slot 582 further including at least two openings, e.g., a distal notch 584 and a proximal notch 585, separated from each other by a distance D along the length of the hub 581 and being formed transversely with respect to the key slot 582 and in communication therewith for engaging a key portion 583 which is connected to the stylet 506 and to a stylet extender handle 586. In FIG. 5A, with the stylet 506 being in the retracted position with respect to the needle 514, the beveled point 530 of stylet 506 is flush with the sharpened point 504 of the needle 514. In this position, the key portion 583 is engaged in the proximal notch 584 In FIG. 5B, via rotation of the extender handle 586, the key portion 583 is disengaged from the proximal notch 584 and via translation along the length of the key slot 582 towards the distal notch 585, the beveled point 530 of the stylet 506 is moved to an extended position equal to dimension D with respect to the sharpened point 504 of needle 514. Upon rotation of the extender handle 586, the key portion 583 is then engaged with the distal key opening 585. To return to the retracted position illustrated in FIG. 5A, the procedure is reversed. Those skilled in the art recognize that the stylet 565 with the shaft portion 560 and curvilinear distal or end portion 561 can be similarly extended and retracted via the extender handle 586 and the hub 581 with the key slot 582, key portion 583, and notches 584 and 585. The foregoing embodiment of the extender handle 586 and the hub 581 with the key slot 582, key portion 583, and notches 584 and 585 ensures accuracy of the pressure monitoring readings and repeatability of locating the pressure sensor at previously monitored positions.

Figure 6:
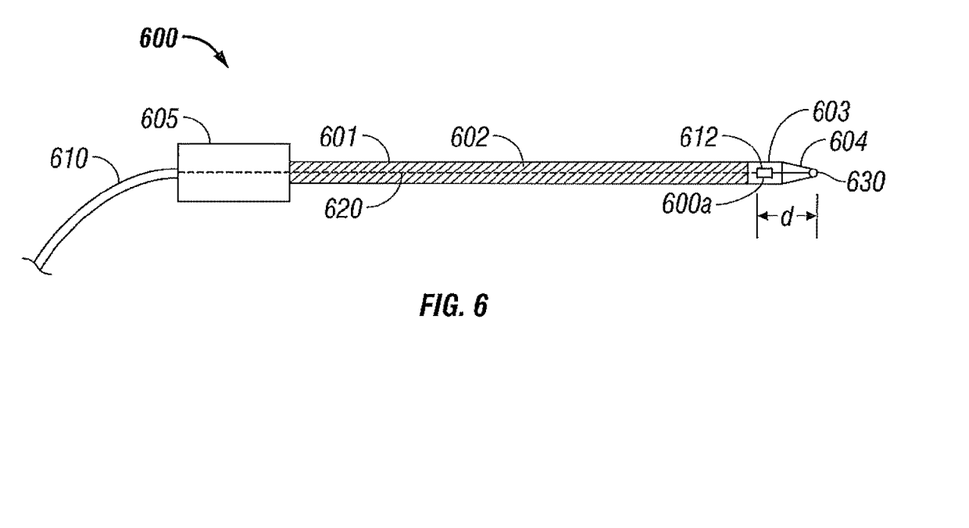
FIG. 6 illustrates an embodiment of the present disclosure of a self-contained needle with pointed tip for tissue penetration and pressure sensing means, radiolucent hub, and external connection cables.

An exemplary embodiment is seen in FIG. 6. For example, FIG. 6 shows an electrode embodiment which requires only one structure to do multiple functions. Probe or probe electrode 600 comprises a shaft 601 which is insulated over its surface 602 and has an exposed tip 603. The tip 603, in this case, is illustrated with a point 604 that has a trocar shape, as opposed to a planar, angular bevel. This merely illustrates that there are a variety of ways of implementing a tissue-piercing point. Disposed at or in proximity to the tip 603 is a pressure sensor 600a for reading the tissue pressure during heating. In particular, in a manner as illustrated previously with respect to FIGS. 1A and 1B, an outer surface of the pressure sensor 600a may be exposed through an aperture 612 in the shaft 601 disposed at a distance "d" upstream from the exposed trocar tip 604 at the distal end of the shaft 601. Pressure sensor 600a instrumentation cable or wire 620 is coupled to the pressure sensor 600a and passes through the shaft 601 either separately from or embedded within cable 610, which may be a multiplexer type cable. In addition, also as discussed previously with respect to FIGS. 1A and 1B, a temperature sensor 630 can be disposed at the exposed uninsulated trocar tip 604 of the shaft 601 and used in conjunction with pressure sensor 600a. The hub 605 is substantially radiolucent so as to enable the possibility of the needle view or tunnel vision radiographic monitoring. The cable 610 connects to the shaft 601, and thus to the exposed tip 603 as a supply of radiofrequency power. This structure can be inserted into the tissue and serve the multiple functions of pressure monitoring, impedance monitoring, RF power delivery, temperature monitoring, etc. Thus, it obviates the need for multiple cannulae and stylets. It has the obvious deficit that, if one wishes to inject contrast media or local anesthetic, it would not be possible without an open lumen needle cannula, as illustrated in FIGS. 2 to 4, or injection and exit holes on the hub and tip of the electrode. However, since injection of such fluids in some situations is not a requirement, the electrode system illustrated in FIG. 6 would be an adequate embodiment of the present disclosure.

Figure 7A:
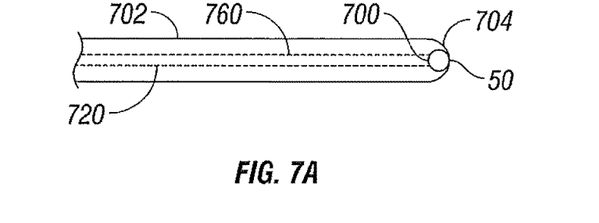
FIG. 7A illustrates a side elevation view of a portion of a single percutaneous electrode including a pressure sensor and a temperature sensor according to a variation of the present disclosure.
Figure 7B:
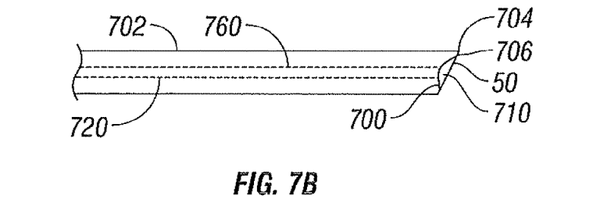
FIG. 7B illustrates a front elevation view of the portion of the single percutaneous electrode of FIG. 7A.

In a variation of the present disclosure, FIGS. 7A and 7B illustrate an electrode 702 having a tip 704 at a distal end and an aperture 710 formed within tip surface 706. The tip surface 706 is formed at an angle resulting in a sharpened point, thereby enabling penetration of bone material by the tip 704. A pressure sensor 700 may be disposed at the distal end in a recessed position internally to the electrode 702 such that the surface of the pressure sensor 700 exposed by the aperture 710 does not protrude beyond the surface 706 of the tip 704. In this variation of the present disclosure, thermocouple 50 may be disposed on surface 706 adjacent to pressure sensor 700 such that measurements of both parameters, i.e., pressure and temperature, are with respect to tissue at the surface 706.

A pressure sensing cable 720 is coupled to the pressure sensor or transducer 700 and, in a manner similar to that previously discussed with respect to FIG. 1, is routed through the multiplexing cable 6 to couple with the pressure monitor 10. A temperature sensing cable 760 is coupled to the thermocouple 50 and also routed through the multiplexing cable 6 to couple with the pressure monitor 10. Those skilled in the art recognize that the foregoing configuration of pressure sensor 700 and thermocouple 50 can substitute for the previously disclosed configurations of pressure sensors and temperature sensors of FIGS. 1, 2, 3, 4, 5, 5A, 5B, and 6 wherein the pressure sensor is disposed at a distance "d" upstream of the tip of the electrode or stylet at the distal end.

This disclosure is not limited to back pain, but may be applied at any of the intervertebral disc levels from the top to the bottom of the spine. For example, it can be used in treating thoracic or neck pain at the appropriate spinal levels. The disclosure is also not restricted to percutaneous needle placement. For example, in the process of doing an open surgical laminectomy, which is a very common procedure, a surgeon may wish to insert such a probe or electrode as has been described herein directly into the exposed disc so that the tip of the probe then resides in the interior of the disc. By this means, radiofrequency or other power sources may be coupled to the electrode so as to heat the intervertebral disc directly under open exposure. Monitoring of the disc pressure and temperature under such conditions can be done directly at the periphery of the disc. The interruption of the neural structures as described above would also pertain for this "open procedure."

Energy therapies as disclosed herein are used also to shrink tissue in many orthopedic applications such as in treating laxities of the shoulder and other joints. Pressure monitoring as disclosed herein may be usefully applied in such orthopedic applications as well.

There are many variations on the present disclosure which might be possible. Combinations of impedance monitoring, stimulating, and temperature monitoring in conjunction with the pressure monitoring and heating method have been described and can be used. How the pressure sensor and the temperature sensor are synchronized with the application of RF energy is dependent on the types of sensors used. Typical thermocouples and pressure transducers use small electrical current for sensing which is easily disrupted by large RF outputs, so the sampling of these sensors is done during RF off times when the duty cycle of these outputs allow. More complicated methods of sampling these sensors during RF on times is possible with filtering, etc. but is expensive to realize.

When the temperatures within the spinal disc rise above the boiling point, the spinal fluids change phase to gas and then the universal perfect gas law generally applies, i.e., $PV=nRT$, (where P is absolute pressure, e.g., in Newtons/meter$^2$ or Pascals, V is volume, e.g., in meter$^3$, n is the number of moles, mol, of gas, R is the universal gas constant in appropriate units, e.g., Joules/mol-degree Kelvin, and T is temperature, e.g. in degrees Kelvin or °K), which can make measurements from the pressure sensor less reliable because areas of phase change do not represent properly the overall tissue pressure. Since optical signal transmission is unaffected by proximate electric or magnetic fields generated by radiofrequency current, the use of optical signal transmission may allow easier adaptation of electrodes for use with magnetic resonance imaging.

It is also not necessary that the source of heating of the disc be radiofrequency current. It could alternatively be microwave current or direct current heating. In the case of direct current heating, one could use for example a nichrome wire inside the probe to create ohmic heat of the tip at a location within the disc. The heat would spread by thermal conduction throughout the disc and give rise to a similar effect on the neural structures as described above. RF heating has advantages in that it deposits the heat energy at longer range relative to the tip, and thus has the feature of distributing the heat throughout the disc in an effective way. The heating may be by penetrating radiation such as ultrasound or microwaves that are absorbed by the disc with or without a probe being placed in the disc. A ferromagnetic seed might be placed in the disc, and it is heated in turn by induction from external waves or beams. Thus, the "probe" may mean any object placed in the disc that is an agent to cause heating of the disc.

The disc heating may be done in conjunction with other intervertebral surgery or instrumentation. For example, the tools that are used during percutaneous discectomy such as a cutting tool may serve also as a heating probe. The disc heating can be done simultaneously or as an adjunct to other disc treatment. This may as well apply to open surgical laminectomy (disc surgery) at which time tools or probes may serve as agents to heat the disc according to the present disclosure.

Stereotactic apparatus and other guidance techniques could be used to place the tip of the electrode at a desired target within the disc or at several targets within the disc in sequence. Clusters of heating probes could be used to more effectively deposit heat throughout a volume of a disc. Such variations are obvious to those skilled in the art and are meant to be included in the scope of the present disclosure.

While the disclosure has been illustrated and described, it is not intended to be limited to the details shown, since various modifications and substitutions can be made without departing in any way from the spirit of the present disclosure. As such, further modifications and equivalents herein disclosed can occur to persons skilled in the art using no more than routine experimentation, and all such modifications and equivalents are believed to be within the spirit and scope of the disclosure as defined by the following claims.

What is claimed:

1. A method of treating back and neck pain of a patient by radiofrequency heating of an intervertebral disc, comprising the steps of:

providing a radiofrequency electrode including proximal and distal ends and having a keyed slot defined therein, the keyed slot including at least two openings separated from each other by a distance along the length of the radiofrequency electrode, the radiofrequency electrode comprising:

a cannula having a proximal end and a distal end and having an open end defined at the distal end thereof, the cannula including a substantially insulated shaft with an uninsulated conductive radiofrequency tip at the distal end thereof, the radiofrequency tip adapted for insertion between intervertebral discs of a patient, the cannula adapted to couple to a power source through a radiofrequency connection attached to the proximal end thereof;

a stylet having a proximal end and a distal end, the stylet fitting into the cannula so that the distal end of the stylet occludes the open end at the distal end of the cannula, the stylet having a key portion configured to operably engage at least one of the openings of the keyed slot, the stylet including a pressure sensor probe proximate the distal end of the stylet, the pressure sensor probe adapted to monitor pressure in the intervertebral disc as the radiofrequency electrode heats the intervertebral disc; and an electrical connection between the radiofrequency connection and the radiofrequency tip, the electrical connection providing electrical communication between the radiofrequency connection and the radiofrequency tip;

inserting the radiofrequency electrode into the body of a patient;

positioning the key portion within a first of the at least two openings of the keyed slot of the radiofrequency electrode;

connecting an external radiofrequency generator to the radiofrequency connection so as to apply a radiofrequency voltage generated by the radiofrequency generator to the radiofrequency tip via the electrical connection;

increasing the radiofrequency voltage to cause current to flow from the radiofrequency tip into the intervertebral disc when the radiofrequency tip is placed therein to cause changes in the intervertebral disc material and nearby neurological structures;

monitoring the pressure in the intervertebral disc using the pressure sensor probe;

and re-positioning the key portion within a second of the at least two openings of the keyed slot of the radiofrequency electrode.

2. A method according to claim 1, wherein immediately following the step of increasing the radiofrequency voltage to cause current to flow from the radiofrequency tip into the intervertebral disc when the radiofrequency tip is placed within the intervertebral disc, the method further comprises the step of turning off the radiofrequency voltage.

3. A method according to claim 2, wherein following the step of turning off the radio frequency voltage, the method further comprises the steps of waiting for a period of approximately one minute and measuring the pressure sensed by the pressure sensor probe.

4. A method according to claim 3, wherein, if it is determined that further treatment is necessary based upon the measured pressure, the method further comprises the steps of:

re-connecting the external radiofrequency generator to the radiofrequency connection so as to apply a radiofrequency voltage generated by the radiofrequency generator to the radiofrequency tip via the electrical connection; and increasing the radiofrequency voltage to cause current to flow from the radiofrequency tip into the intervertebral disc when the radiofrequency tip is placed within the intervertebral disc.

5. A method according to claim 1, wherein the pressure sensor probe includes an aperture defined therein and a pressure sensor that is at least partially exposed through the aperture to thereby sense pressure in the disc.

6. A probe electrode comprising:

a hub, the hub having a keyed slot defined therein that extends along a portion of the length of the hub;

a cannula having a proximal end and a distal end and having an open end defined at the distal end thereof, the cannula having a radiofrequency tip at the distal end thereof, the cannula adapted to couple to a power source;

the hub and the cannula defining a needle; and a stylet having a proximal end and a distal end, the stylet fitting into the cannula so that the distal end of the stylet occludes the open end at the distal end of the cannula, the stylet having a key portion, the stylet including a pressure sensor proximate the distal end of the stylet, the pressure sensor adapted to communicate with a pressure monitoring apparatus so as to measure the pressure of the intervertebral disc, wherein the keyed slot of the hub includes at least two openings that are separated from each other by a distance along the length of the hub, the at least two openings configured to operably engage the key portion of the stylet.

7. A probe electrode according to claim 6, wherein the stylet includes an electrical connector adapted to connect the radiofrequency tip to a power generator for generating heat at the distal end of the cannula.

8. A probe electrode according to claim 6, wherein the cannula has a lumen defined therein and the stylet includes a shaft configured for variable insertion within the lumen through the proximal end of the cannula such that the position of the pressure sensor can be varied within the lumen of the cannula.

9. A probe electrode according to claim 6, wherein the pressure sensor monitors pressure at a position in the intervertebral disc.

10. A probe electrode according to claim 8, wherein the pressure sensor monitors pressure at a plurality of positions in the intervertebral disc and the stylet is selectively movable to an extended position equal to the distance along the hub wherein the key portion engages the keyed slot via one of the at least two openings.

11. A probe electrode according to claim 6, wherein the stylet includes an aperture defined therein and the pressure sensor is at least partially exposed through the aperture to thereby sense pressure in the disc.

* * * * *